(12) United States Patent
Studer et al.

(10) Patent No.: US 6,527,805 B2
(45) Date of Patent: Mar. 4, 2003

(54) INTERVERTEBRAL IMPLANT

(75) Inventors: Armin Studer, Winterthur (CH); Silvio Rudolf Schaffner, Berlingen (CH); Albert Maria Vodermayer, Dietlikon (CH); Gudrun Grimberg, Winterthur (CH); Jens Christian Kärger, Winterthur (CH); Hans Erlach, Winterthur (CH)

(73) Assignee: Sulzer Orthopedics LTD, Baar (CH)

( * ) Notice: Subject to any disclaimer, the term of this patent is extended or adjusted under 35 U.S.C. 154(b) by 0 days.

(21) Appl. No.: 09/733,828

(22) Filed: Dec. 8, 2000

(65) Prior Publication Data

US 2001/0012966 A1 Aug. 9, 2001

(30) Foreign Application Priority Data

Dec. 15, 1999 (EP) .............................. 99811163

(51) Int. Cl.[7] .................................................. A61F 2/44
(52) U.S. Cl. .................................. 623/17.16; 623/17.11
(58) Field of Search ........................... 623/17.11–17.16

(56) References Cited

U.S. PATENT DOCUMENTS

| 5,084,051 | A |   | 1/1992 | Toermaelae |
| 5,192,327 | A |   | 3/1993 | Brantigan |
| 5,429,863 | A |   | 7/1995 | McMillin |
| 5,766,253 | A |   | 6/1998 | Brosnahan |
| 6,074,423 | A |   | 6/2000 | Lawson |
| 6,241,770 | B1 | * | 6/2001 | Michelson ............... 623/17.11 |

FOREIGN PATENT DOCUMENTS

WO     WO 00/51529     9/2000

* cited by examiner

Primary Examiner—David J. Isabella
Assistant Examiner—Thomas Barrett
(74) Attorney, Agent, or Firm—Townsend and Townsend and Crew LLP

(57) ABSTRACT

An intervertebral implant (1) with a hollow cylindrical shape is provided with an outer thread (2) for screwing the implant into the intermediate space between two adjacent vertebrae. The implant (1) is provided with openings (3) in its wall through which bone can grow into the implant (1), with the implant (1) being manufactured of a material which is transparent for X-rays.

12 Claims, 5 Drawing Sheets

Figure 3:
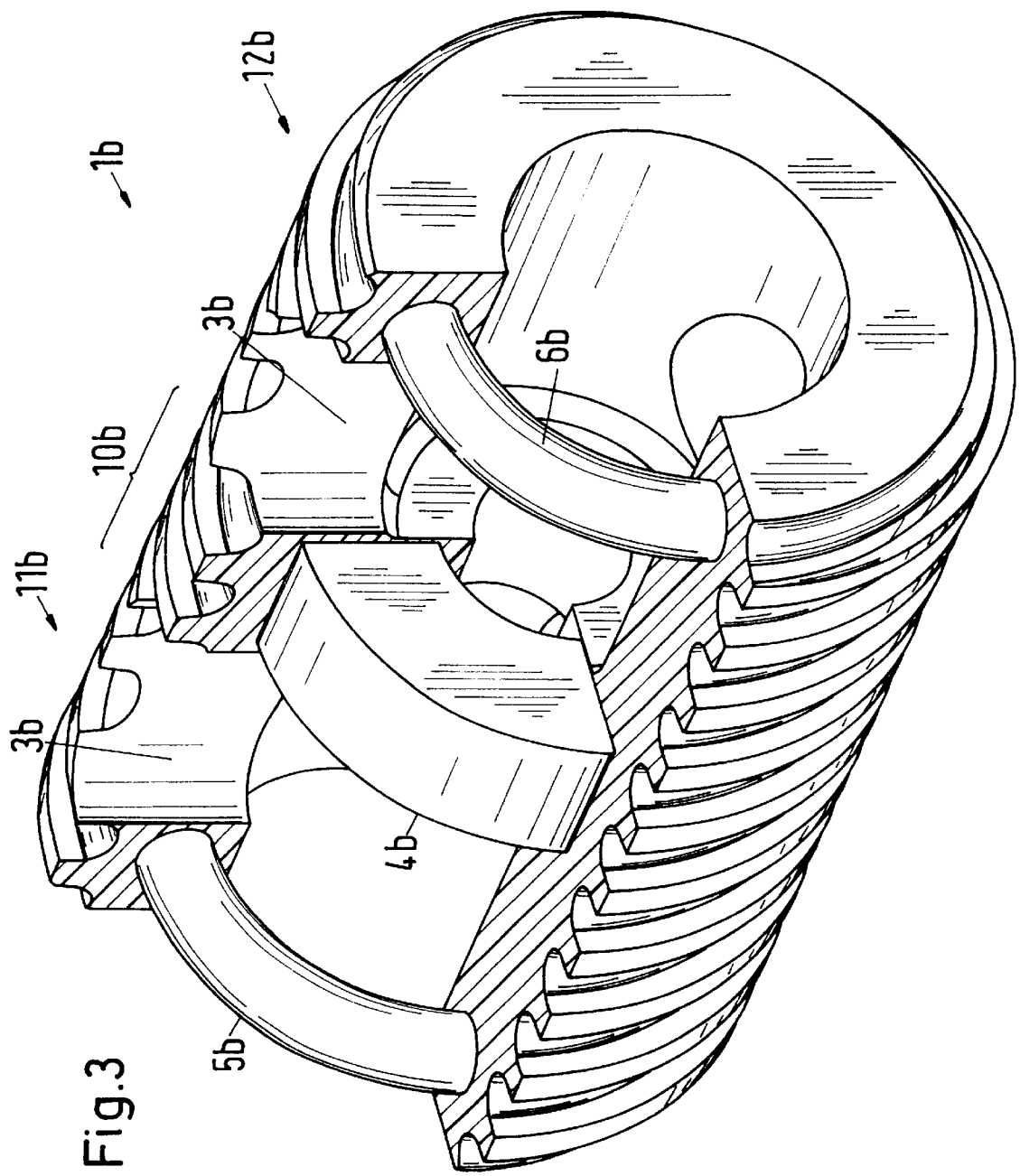

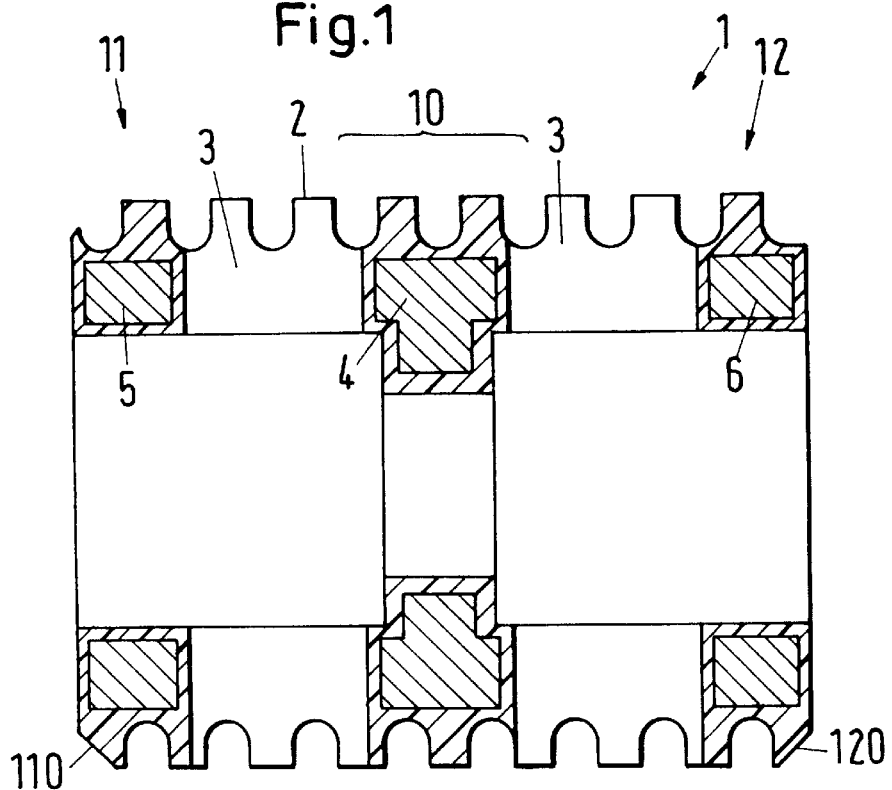
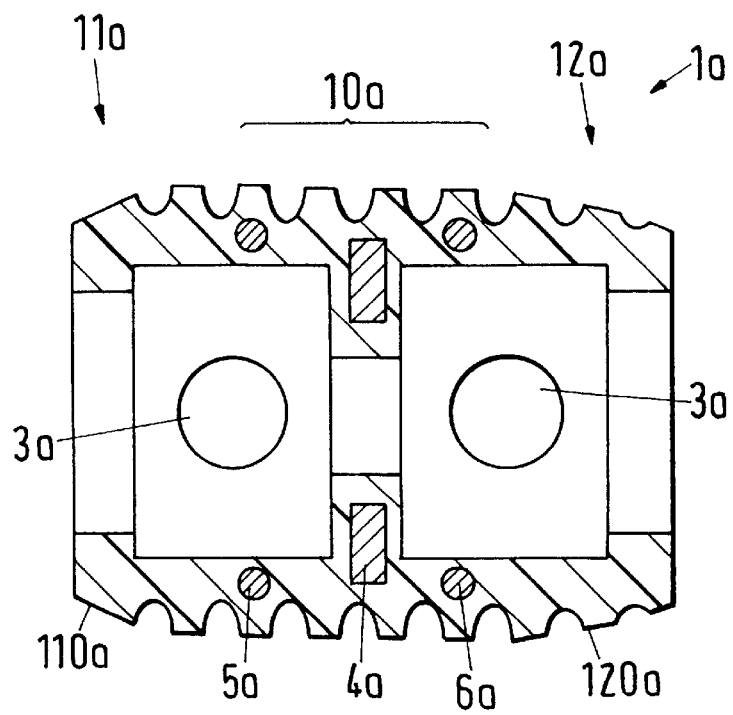

INTERVERTEBRAL IMPLANT

The invention relates to an intervertebral implant in accordance with the independent patent claim.

Intervertebral implants exist in many different embodiments. As their name indicates, they are implanted between two adjacent vertebrae and are used in particular when the intervertebral disc which is arranged there is not capable of functioning or is highly impaired in its functioning. A possible and relatively frequently chosen kind of treatment for such illnesses is to remove the vertebral disc or parts of it and to grow together (fusion) the two mutually adjacent vertebrae between which the damaged vertebral disc is or was arranged. In order to further the growing together of the vertebrae the implant can be filled with bone shavings or bone substitute material. The fusion of the adjacent vertebrae should take place in such a manner that the vertebrae have their normal distance from one another during and after the growing together as if the intact intervertebral disc were still present, because otherwise the functioning of the spinal column as a whole can be considerably impaired.

The implant serves for attaining the primary stability in the first phase after the implantation and must in this phase take up the stresses which would act on an intact intervertebral disc. After a time duration of typically six to nine months the secondary stability is achieved in that the bone of the two adjacent vertebrae has grown together (fused) through the implant, so that the two adjacent vertebrae are arranged with a normal spacing with respect to one another, as if an intact vertebral disc were still present between them. The two adjacent vertebrae are however firmly connected (fused) to one another and can take up the stresses.

For maintaining the distance of two adjacent vertebrae from one another during the first phase after the implantation, that is, during the phase in which the bones of the adjacent vertebrae have not yet grown together (fused), there are various implants and also different operating techniques which already differ already through the manner of the access to the spinal column—from the anterior or from the posterior.

Thus for example an intervertebral implant is known from U.S. Pat. No. 5,192,327 which is formed as an oval ring-like element. A plurality of elements of this kind can be put together to form a column, the longitudinal axis of which extends after the implantation approximately in the direction of the spinal column, in order also to be able where appropriate to replace a vertebra. The end sides of this implant are open so that bone can grow in into the implant and a bone fusion can take place. The implant can be filled with bone shavings or bone substitute material for furthering the bone fusion. A plastic material which is reinforced by carbon fibers is proposed for this implant in order to be able to monitor with the help of X-rays the progress of the growing together of the bones of the adjacent vertebrae inside the implant. The titanium which is frequently used for implants of this kind does not permit a monitoring of the progress during the growing together of the bone of the two vertebrae inside the implant, since the implant of titanium is not transparent for X-rays.

The implant which is described in U.S. Pat. No. 5,192,327 is principally suitable for the implantation with an anterior access. Otherwise, it is the case in this implant that the implant can frequently not ensure the required primary stability alone and thus further fasteners or stabilizers respectively which must be connected to the vertebrae (e.g. by means of pedicular screws) become necessary in addition to the implant in order to ensure the required primary stability after the operation and in order not to endanger the success of the operation. If then after several months the secondary stability is achieved (through the growing together of the vertebrae) then the additional fasteners or stabilizers respectively can be removed in a further operation.

In order to avoid the application of additional fasteners or stabilizers respectively, which make the operation more complicated (and also more cost intensive) and which can moreover later be removed by means of a further operation, hollow cylindrical implants (so-called "cages") have already been proposed, for example in U.S. Pat. No. 5,015,247, which are screwed in between adjacent vertebrae with their longitudinal axis transverse to the direction of the spinal column. These hollow cylindrical implants are provided with an outer thread which cuts itself in with the thread into the two vertebral bones between which the implant is inserted during the screwing in. Through this the implants are secured against a sliding out. The implants are provided in the wall with openings (holes), so that bone can grow through the implant, so that a bone connection (fusion) of the two vertebrae can come about after several months.

These implants—the cages—have the advantage that they are the only implants which are required during the operation; that is, no additional fasteners or stabilizers are required. A further operation at a later time point for the removal of additional fasteners or stabilizers respectively is thus not necessary. In addition in the use of implants of this kind the access both from the anterior and from the posterior is relatively uncomplicated from the point of view of the surgical technique.

Previously cages of this kind have been manufactured of coarsely blasted titanium, since on the one hand the correspondingly porous titanium surface furthers the growing in or the growing on respectively of bone, but has above all however the required stability on the one hand; on the other hand however it also has a certain elasticity in order to be able to reliably take up the stress acting on the implant in the first phase of the operation, so that additional fasteners or stabilizers respectively are not required. Disadvantageous is that the progress of the bone fusion inside the cages can practically not be monitored in cages of this kind.

The object of the invention is therefore to propose a hollow cylindrical intervertebral implant of this kind (a "cage") which is on the one hand alone suitable for taking up the stresses acting on the implant in the first phase of the operation, but is at the same time however suitable for enabling a monitoring of the bone fusion through imaging processes (X-rays, MRI, CT, etc.) inside the implant.

This object is satisfied by the intervertebral implant which is characterized by the features of the independent patent claim. Particularly advantageous embodiments result from the features of the subordinate patent claims.

This object is satisfied in particular by an intervertebral implant with a hollow cylindrical shape, said implant being provided with an outer thread for screwing in the implant into the intermediate space between two adjacent vertebrae. The implant is provided with openings in its wall through which bone can grow in into the implant, with the implant being manufactured of a material which is transparent for X-rays.

The implant in accordance with the invention has the advantages that on the one hand it can take up the stresses acting on the implant in the first phase after the operation, that it is the only implant and no additional fasteners or stabilizers are required, that the access is possible in a relatively simple way both from the anterior and from the posterior, and that the progress of the bone fusion inside the implant can be monitored with the help of X-ray investigations or other imaging methods (MRI, CT, etc.).

In an advantageous exemplary embodiment of the implant in accordance with the invention the material which is transparent for X-rays is a plastic and can even be manufactured of a plastic only. This plastic can for example be present in a fiber form and be wound to form the desired shape of the implant and then be subjected to a compression sintering. An implant of this kind has no additional reinforcement fibers, but rather can be manufactured of the plastic fibers themselves. In the compression sintering the basic orientation of the plastic molecules of the fibers is preserved, through which the stiffness is imparted to the implant; the fibers are however melted during the compression sintering to such an extent that they combine with one another and form a firm compound in the shape of the implant.

In an advantageous exemplary embodiment of the implant in accordance with the invention the material which is transparent for X-rays comprises a plastic which is reinforced with fiber material.

In this, different variants come under consideration, as will be explained in detail. Thus for example endless fiber reinforced plastics ("tapes") can be wound and then pressed and where appropriate the thus manufactured body also surrounded by a plastic. With quasi endless fiber reinforced materials ("commingled stretch broken yarn")—these are materials in which the endless fibers are broken, but commingled with one another in order to impart a certain longitudinal elasticity to the material—it is likewise possible to wind and then to press and then to surround the thus manufactured body where appropriate with a plastic. In so-called long fiber reinforced plastics (fiber lengths typically in the range from 3 mm up to 6 mm or even 10 mm) the discrete fibers are already present in the plastic and the implant is manufactured e.g. through extrusion. Finally, short fiber reinforced plastics also come under consideration (fiber lengths typically in the range from 0.1 mm to 0.4 mm), which can in particular be processed to form the implant in injection moldable plastics. Further advantageous variants can also result from the combination of the different manufacturing techniques.

The named materials are particularly suitable for taking up the loads which act on the implant immediately after the operation and are naturally transparent for X-rays, so that the progress of the bone fusion inside the implant can be monitored with the help of X-ray investigations.

In a further development of the implant the plastic is an injection moldable plastic. The injection molding technique permits a reliable and at the same time economical manufacture of the implant.

The fiber material advantageously comprises carbon fibers and the plastic is preferably polyether ether ketone (PEEK). The carbon fibers take up the loads arising immediately after the operation in a reliable way and can be injection cast in polyether ether ketone because this is an injection moldable plastic which is also biocompatible in addition.

In an advantageous exemplary embodiment of the implant in accordance with the invention the implant comprises a hollow cylindrical body of fiber material which is embedded in plastic, with the hollow cylindrical body of fiber material extending over the entire length of the implant. This exemplary embodiment is distinguished in that the taking up of the load can take place practically over the entire length of the implant and thus the stress on the implant can be distributed over a relatively large area.

In another exemplary embodiment of the implant the implant comprises three bodies which are manufactured of fiber material, which are formed in ring shape and which are embedded in plastic. The taking up of the load takes place in the region of the bodies which are formed in ring shape and can be distributed differently over the length of the implant.

In a first variant with three such bodies which are formed in ring shape, one of the bodies which are formed in ring shape is arranged in the central region of the implant and the other two in the respective end region of the implant. This allows a stressing of the implant both in the central region and in the end regions.

In a further variant all three ring-shaped bodies are arranged more or less in the central region of the implant. The end regions of the implant are in each case provided with a chamfer. The taking up of the load takes place in this variant more or less exclusively in the central region, for which reason all ring-shaped bodies are arranged in this region. This is the case because the end region is provided with a chamfer and in a first phase after the operation has no contact there with the bone which takes up the load. The taking up of the load should thus intentionally take place in the central region in this exemplary embodiment. The chamfer in the end regions facilitates the rotating in of the implant during the operation.

In a further exemplary embodiment of the implant in accordance with the invention the implant comprises a body of fiber material which winds uniformly helically around the longitudinal axis of the implant and which is embedded in plastic, and indeed in such a manner that the ridges of the outer thread of the implant are arranged around the windings of the helical body and the base of the outer thread is arranged between the windings of the helical body. The ridges of the outer thread are thus so to speak reinforced by the helically winding body of fiber material, through which a particular stability is imparted to the thread. In addition the helically winding body of fiber material also ensures a taking up of the load over the entire length of the implant.

Finally, in all above named exemplary embodiments the surface of the implant can be provided with a layer which furthers the osteo-integration, in particular with a hydroxylapatite ceramic layer.

Figure 4:
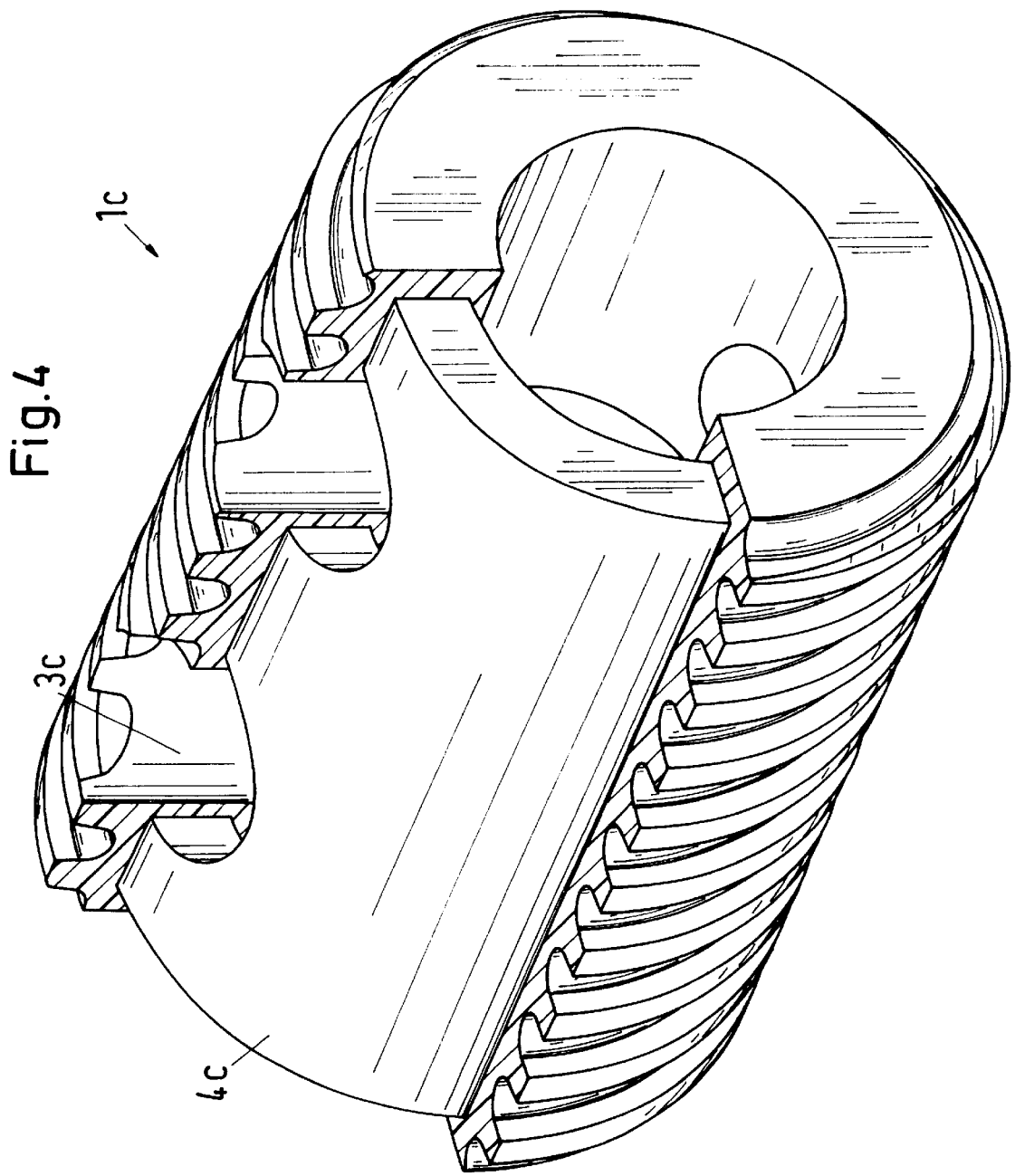
Figure 5:
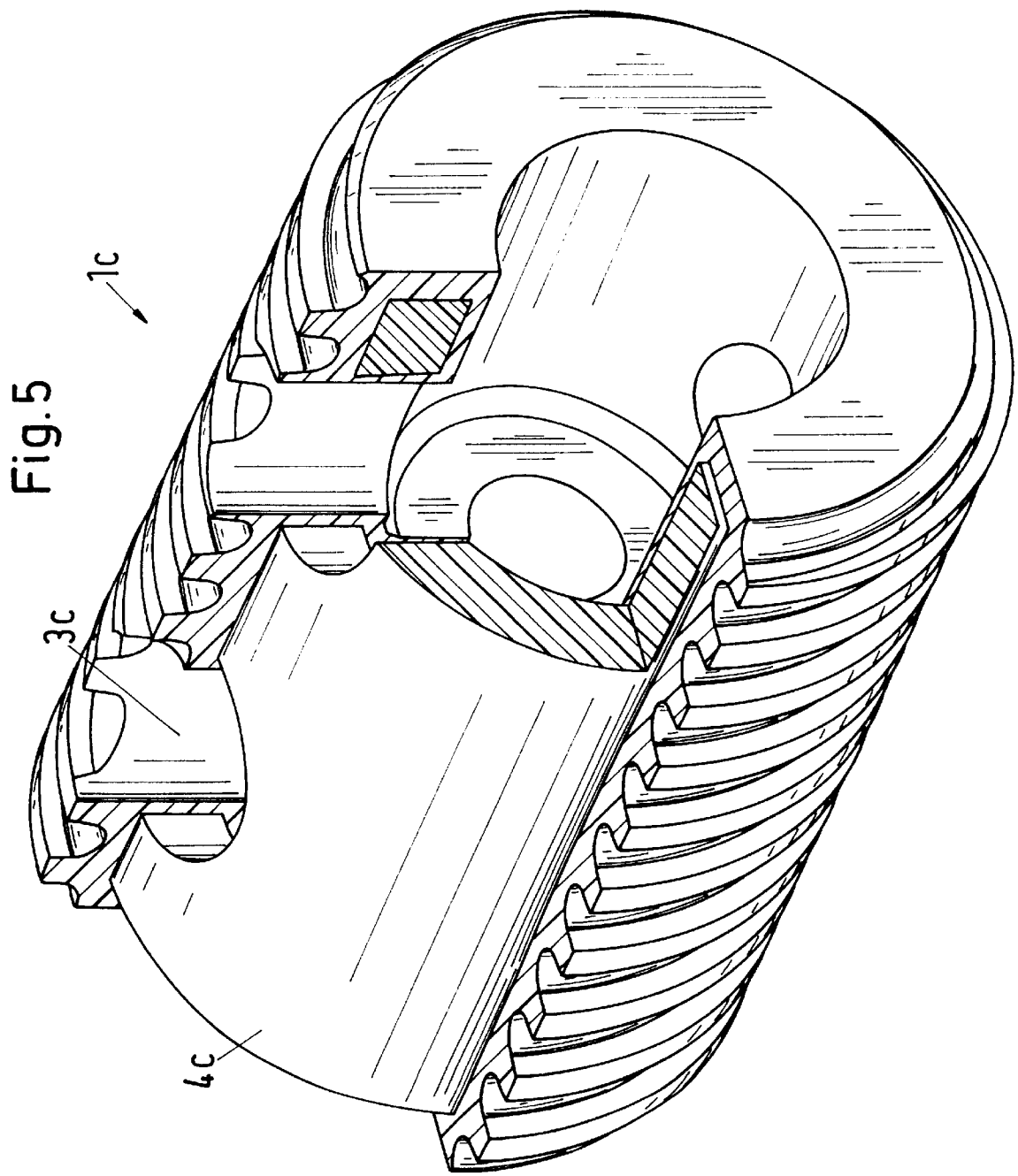
Figure 6:
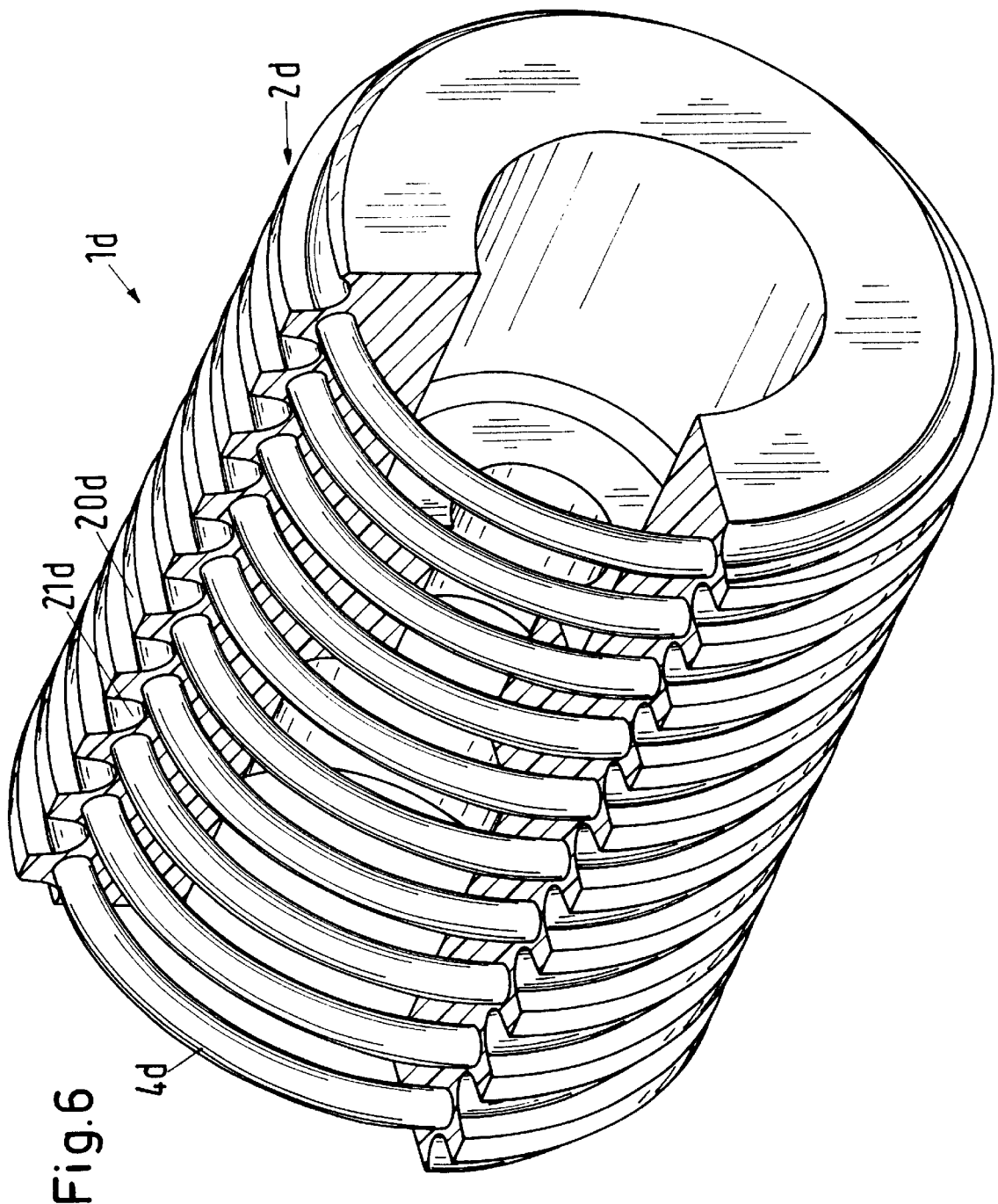

The invention will be explained in the following with reference to the drawings; in which represents, partly greatly enlarged and schematically and/or in section:

FIG. 1 a first exemplary embodiment of an intervertebral implant in accordance with the invention with three ring-shaped bodies of fiber material, one in the central region and the other two in the respective end region, FIG. 2 a second exemplary embodiment of an implant in accordance with the invention with three ring-shaped bodies of fiber material, which are all arranged in the central region of the implant however, FIG. 3 a third exemplary embodiment of an implant in accordance with the invention with three ring-shaped bodies of fiber material, one in the central region and the other two in the respective end region, with the body in the central region having a rectangular cross-section and the two bodies in the end regions having a circular cross-section, FIG. 4 a fourth exemplary embodiment of an implant in accordance with the invention with a hollow cylindrical body of fiber material, FIG. 5 the exemplary embodiment of FIG. 4 in a different illustration and FIG. 6 a fifth exemplary embodiment of an implant in accordance with the invention with a helically winding body of fiber material.

In FIG. 1 one recognizes a first exemplary embodiment of an intervertebral implant 1 in accordance with the invention which is provided with an outer thread 2 in order that the implant 1 can be screwed in between two vertebrae (not illustrated). The implant 1 has a hollow cylindrical shape and is provided in its wall with openings 3 through which bone can grow through into the implant 1. The implant 1 has three ring-shaped bodies 4, 5, 6 of fiber material, of which the body 4 is arranged in the central region 10 and the two bodies 5 and 6 are arranged in the two end regions 11 and 12 of the implant 1. The ring-shaped bodies 4, 5, 6 are surrounded by a plastic. In the end regions one recognizes a very slight chamfer 110 and 120 respectively, which serve for the easier screwing in of the implant 1. The ring-shaped body 4 in the central region 10 of the implant 1 is executed to be somewhat stronger than the two ring-shaped bodies 5 and 6 in the end regions 11 and 12 of the implant 1 since the greater stressing of the implant 1 takes place in the central region 10. The exemplary embodiment shown in FIG. 1 can be stressed both in the central region 10 and in the two end regions 11 and 12 and is also in contact there with the surrounding bone matter in a manner which takes up loads.

The implant 1 can be manufactured for example in that first the ring-shaped bodies 4, 5, 6 are wound from an endless fiber reinforced plastic as fiber material, are then subjected to a compression sintering and are then introduced in a defined position into an injection molding form where the compression sintered ring-shaped bodies 4, 5, 6 are injection molded into plastic (e.g. PEEK). In this way there arises an implant 1 in which the progress of the bone fusion can be well monitored with the help of X-rays.

In the second exemplary embodiment in accordance with FIG. 2 the implant 1a likewise comprises three ring-shaped bodies 4a, 5a, 6a of fiber material (e.g. of an endless fiber reinforced plastic), with however all three ring-shaped bodies 4a, 5a, 6a being arranged more or less in the central region 10a of the implant 1a. The end regions 11a and 12a are in each case provided with a clearly pronounced chamfer 110a and 120a respectively. These chamfers 110a and 120a respectively serve for the considerable facilitation during the screwing in of the implant 1a, but they are not in contact with the bone after the operation in a manner which takes up loads. The implant 1a must thus take up more or less the entire load in the central region 10a, for which reason the implant is also provided there with three ring-shaped bodies 4a, 5a, 6a. In addition one also recognizes in FIG. 2 the openings 3a, through which the bone can grow in into the implant 1a. The manufacture can take place analogously as in the exemplary embodiment in accordance with FIG. 1, with however the openings 3a being produced after the first injection process (e.g. through boring or milling) and then where appropriate a further injection process taking place in order that parts of the fiber material do not happen to enter into the body.

In FIG. 3 a third exemplary embodiment of an implant 1b in accordance with the invention is illustrated. In this implant 1b three ring-shaped bodies 4b, 5b, 6b of fiber material (e.g. of an endless fiber reinforced plastic) can again be recognized, with the body 4b being arranged in the central region 10b and the other two bodies 5b, 6b being arranged in the end region 11b and 12b respectively. Furthermore, one recognizes the openings 3b, through which the bone can grow in into the implant 1b, so that a fusion can come about. The cross-section of the ring-shaped bodies can in each case be matched to the other circumstances, in particular to the desired load take-up and to the space which is available for the injection molding into plastic (e.g. PEEK) respectively.

In the exemplary embodiment which is shown in FIG. 3 the ring-shaped body 4b which is arranged in the central region 10b has a rectangular cross-section, whereas the bodies 5b and 6b which are arranged in the end regions have a circular cross-section. The manufacture can take place in analogy with the exemplary embodiment in accordance with FIG. 1.

A fourth exemplary embodiment of an implant 1c in accordance with the invention is illustrated in FIG. 4 and FIG. 5. This exemplary embodiment of the implant 1c comprises a hollow cylindrical body 4c of fiber material (e.g. of an endless fiber reinforced plastic) which is embedded in plastic (e.g. PEEK). The hollow cylindrical body 4c extends over the entire length of the implant 1c and is likewise provided with openings 3c, through which bone can grow in into the implant 1c. Through the fact that the hollow cylindrical body 4c of fiber material extends over the entire length of the implant 1c a load take-up can take place over the entire length of the implant in the first phase after the operation. Accordingly, a very small chamfer at best is also provided in both end regions of the implant 1c in order to facilitate the screwing in.

The implant 1c can for example be manufactured in such a manner that the hollow cylindrical body is first wound of fiber material and is then subjected to a compression sintering. In so far as the fiber material permits, the openings 3c can be produced afterwards and then the hollow cylindrical body 4c, having been provided with the openings 3c, can be introduced into an injection mold and be injection molded into plastic. If the fiber material does not permit the production of the openings 3c prior to the casting, the hollow cylindrical body 4c is first injection molded into the plastic and then the openings 3c are produced through boring or milling respectively. In order that the fiber material can not come into contact with the bone or other body tissue or enter into the blood vessels, a second injection molding process then takes place in which an injection molding around the fiber material takes place at least in the region of the openings 3c so that the fiber material of the hollow cylindrical body 4c can not come into contact with the bone after the second injection molding process.

In FIG. 6 a fifth exemplary embodiment of an intervertebral implant 1d in accordance with the invention is shown. This exemplary embodiment of the implant id comprises a body 4d of fiber material (e.g. of endless fiber reinforced plastic) which winds uniformly helically around the longitudinal axis of the implant 1d. This body 4d is embedded in plastic (e.g. PEEK) and indeed in such a manner that the windings of the helical body 4d come to lie in the ridges 20d of the outer thread 2d. Accordingly the base 21d of the outer thread 2d comes to lie between the windings of the helical body 4d. The ridges 21d of the outer thread 2d are thus reinforced by the helical body 4d. The taking up of the load after the implantation likewise takes place in this exemplary embodiment over the entire length of the implant 1d, for which reason the implant 1d is provided with a very small chamfer at best in order to facilitate the screwing in of the implant 1d. The openings for the growing in of the bone into the implant are not illustrated here for reasons of draftsmanship, but could however be produced in a manner similar to that which has already been described.

As far as the materials for all described exemplary embodiments are concerned, the following fibers in particular come under consideration as fibers for the fiber material: organic fibers such as e.g. aramide and PBO fibers (poly(p-phenylene-2,6,-benzobisoxazole) as well as inorganic fibers such as e.g. carbon fibers, aluminum oxide fibers, zircon oxide fibers and boron fibers. The fiber material are then preferably thermoplastic matrices of such fibers and a thermoplastic plastic, such as e.g. the already named PEEK (polyether ether ketone), but also plastics such as PES (polyether sulphone), PSU (polysulphone), PET (polyethylene terephthalat)), UHMWPE (ultra high molecular weight polyethylene), PEI (polyether imide). A thermosetting plastic matrix of EP (epoxy resin) is also possible.

It is likewise conceivable that the implant is not provided with a body of fiber material of any winding of whatever kind, but that the fibers are embedded as cut or broken fibers respectively in the plastic (short fiber reinforced plastics, long fiber reinforced plastics, "commingled stretch broken yarn", see above) and that the implant is manufactured of such a plastic which is reinforced with fiber material as a starting material, which is embedded in one of the named plastics. As already mentioned above, the surface of the implant can also be provided with a thin-walled coating which furthers the osteo-integration of the implant, in particular with a hydroxylapatite ceramic layer.

What is claimed is:

1. Intervertebral implant comprising a material which is transparent for X-rays and which has a hollow cylindrical shape provided with an outer thread for screwing the implant into an intermediate space between two adjacent vertebrae, the implant forming a wall having openings through which bone can grow into the implant, the implant having first, second and third ring-shaped bodies made of fiber material embedded in plastic.

2. Intervertebral implant in accordance with claim 1, in which the material which is transparent for X-rays comprises a plastic.

3. Intervertebral implant in accordance with claim 2, in which the plastic is an injection moldable plastic.

4. Intervertebral implant in accordance with claim 1, in which one of the ring-shaped bodies is arranged in a central region of the implant and the other ring-shaped bodies are arranged in respective end regions of the implant.

5. Intervertebral implant in accordance with claim 1, in which all ring-shaped bodies are arranged in a central region of the implant and in which the end regions of the implant are provided with a chamfer.

6. Intervertebral implant in accordance with claim 1, in which a surface of the implant is provided with a thin coating of a material which furthers osteo-integration.

7. Intervertebral implant according to claim 6 wherein the thin coating of a material which furthers osteo-integration comprises hydroxylapatite ceramic.

8. Intervertebral implant comprising a hollow cylindrical shape provided with an outer thread for screwing the implant into an intermediate space between two adjacent vertebrae, the implant forming a wall having openings through which bone can grow into the implant, the implant including a body of fiber material which winds uniformly helically around a longitudinal axis of the implant and which is embedded in plastic so that ridges of the outer thread of the implant are arranged about the windings of the helical body and a base of the outer thread is arranged between the windings of the helically wound body.

9. Intervertebral implant in accordance with claim 8, in which the material which is transparent for X-rays comprises a plastic which is reinforced by a fiber material.

10. Intervertebral implant in accordance with claim 9, in which the fiber material comprises carbon fibers and the plastic is polyether ether ketone (PEEK).

11. Intervertebral implant comprising a material which is transparent for X-rays and which has a hollow cylindrical shape provided with an outer thread for screwing the implant into an intermediate space between two adjacent vertebrae, the implant forming a wall having openings through which bone can grow into the implant, the material which is transparent for X-rays comprising a plastic which is reinforced by a fiber material, the implant comprising a hollow cylindrical body of fiber material embedded in plastic and extending over substantially the entire length of the implant.

12. Intervertebral implant according to claim 11 including a hydroxylapatite ceramic layer on the exterior of the implant.

* * * * *